US00PP31743P2

(12) United States Plant Patent
McConachie

(10) Patent No.: US PP31,743 P2
(45) Date of Patent: May 12, 2020

(54) ***MACADAMIA* TREE NAMED 'MCT1'**

(50) Latin Name: ***Macadamia integrifolia* Maiden et Betche**
Varietal Denomination: MCT1

(71) Applicant: Macadamia Conservation Trust, Lismore, New South Wales (AU)

(72) Inventor: Ian McConachie, Pie Creek (AU)

(73) Assignee: Macadamia Conservation Trust, Linsmore, New South Wales (AU)

( * ) Notice: Subject to any disclaimer, the term of this patent is extended or adjusted under 35 U.S.C. 154(b) by 0 days.

(21) Appl. No.: 16/501,223

(22) Filed: Mar. 8, 2019

(51) Int. Cl.
*A01H 5/10* (2018.01)
*A01H 6/00* (2018.01)

(52) U.S. Cl.
USPC ..... Plt./152

(58) Field of Classification Search
USPC ..... Plt./152

CPC ..... A01H 5/08; A01H 5/0825; A01H 5/00; A01H 6/00; A01H 6/54; A01H 5/10
See application file for complete search history.

(56) References Cited

PUBLICATIONS

ANFIC 2019 MCT1 *Macadamia*, [retrieved on Nov. 13, 2019], [online] retrieved from the Internet at https://www.anfic.com.au/variety/mct1-macadamia/, 5 pp. total (Year: 2019).*
MPC 9/18 The Nutshell MPC's News letter for *Macadamia* Growers, [retrieved on Nov. 13, 2018], [online] retrieved from the Internet at https://mpcmacs.com.au/media/Nutshell-September-2018.pdf, pp. 1-13 (Year: 2018).*

* cited by examiner

*Primary Examiner* — June Hwu
(74) *Attorney, Agent, or Firm* — Michelle Bos Legal LLC

(57) ABSTRACT

A new and distinct variety of *macadamia* tree named 'MCT1' notable for its precocity, high yield, relatively thin shell and husk, and excellent nut quality as compared to other *macadamia* cultivars.

6 Drawing Sheets

Latin name: *Macadamia integrifolia* Maiden et Betche.
Variety denomination: 'MCT1'.

BACKGROUND OF THE VARIETY

'MCT1' is a new and distinct variety of *macadamia* tree that originated as the product of an open cross of unknown parents near Wolvi, Queensland, Australia in 1982. 'MCT1' was first asexually propagated by budding onto seedling rootstock (not patented) at Wolvi in 1989. The new variety has been asexually reproduced over multiple generations and has been observed to remain true to type, retaining its desirable characteristics.

BRIEF DESCRIPTION OF THE VARIETY

'MCT1' was first selected for its precocity, high yield, relatively thin shell and husk, and excellent kernel quality as compared to other *macadamia* cultivars. It is distinguished from known *macadamia* variety 'A16' (not patented) by its leaves and fruit, as described in Table 1 below.

TABLE 1

Comparison of 'MCT1' Macadamia Tree to 'A16' Macadamia Tree

| | 'A16' | 'MCT1' |
|---|---|---|
| Tree height | Short | Medium |
| Leaf margin serration | Smooth serration with few spines | Serrated margin with many spines |

TABLE 1-continued

Comparison of 'MCT1' Macadamia Tree to 'A16' Macadamia Tree

| | 'A16' | 'MCT1' |
|---|---|---|
| Leaf margin undulation | No undulations | Undulations present |
| Kernel shape | Oval | Globose |
| Position of hilum | Raised | Not raised |
| Husk thickness | Thick | Thin |

BRIEF DESCRIPTION OF THE PHOTOGRAPHS

The attached photographs were taken in February 2019 at Gympie, Queensland, Australia. The trees depicted are about 9 years old.

DETAILED BOTANICAL DESCRIPTION OF THE VARIETY

The following-detailed botanical description is based on observations made during the 2019 growing season at Gympie, Queensland, Australia of nine-year-old 'MCT1' *macadamia* trees grown on 'H2' rootstock. All colors are described according to The Royal Horticultural Society Colour Chart (1995). The characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

DETAILED BOTANICAL DESCRIPTION

Figure 1:
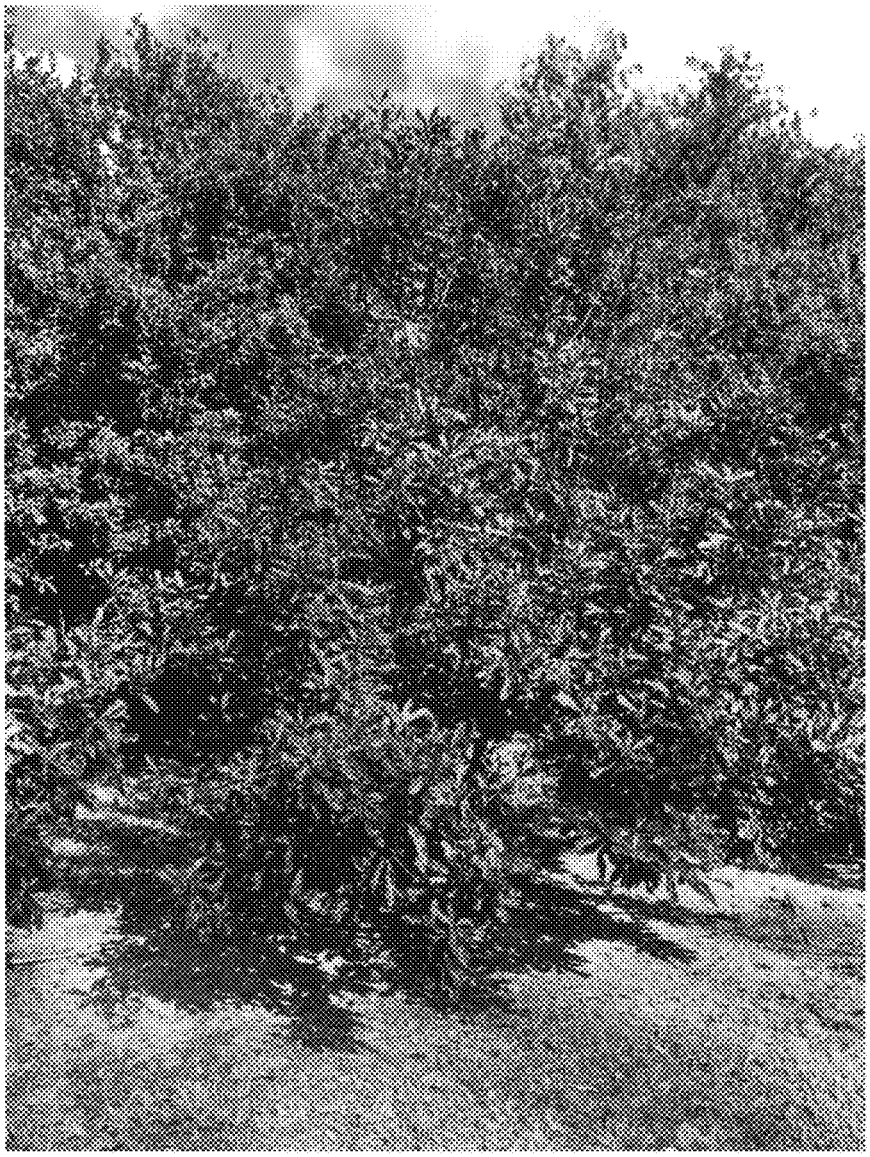
FIG. 1 shows an 'MCT1' *macadamia* tree.
Figure 2:
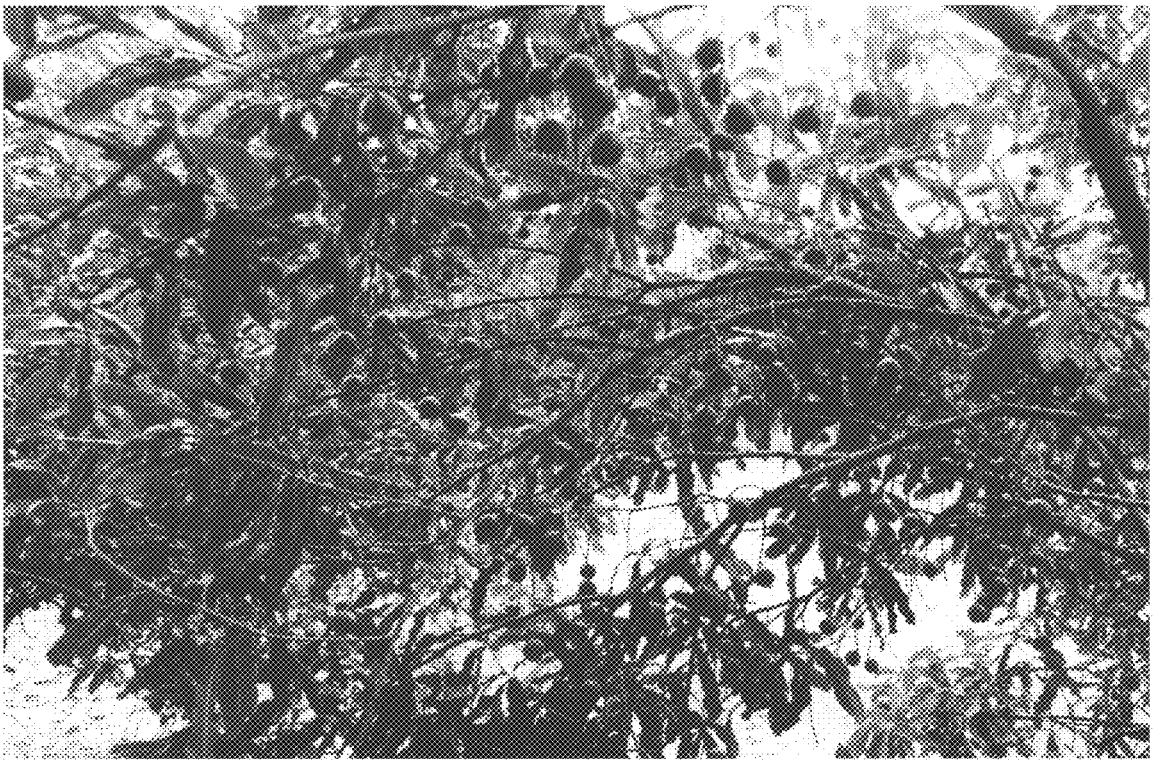
FIG. 2 shows the branches, leaves and fruit of an 'MCT1' *macadamia* tree.
Figure 3:
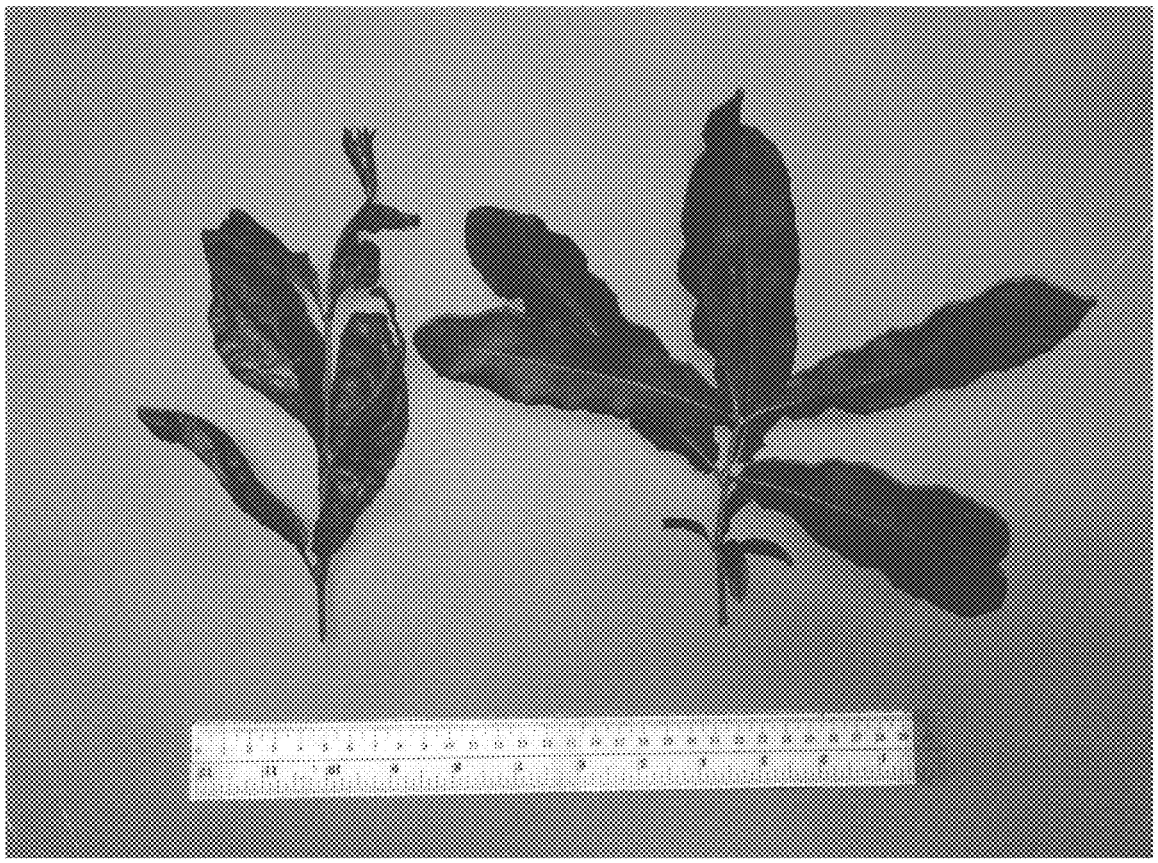
FIG. 3 shows young (left) and mature (right) leaves of an 'MCT1' *macadamia* tree.
Figure 4:
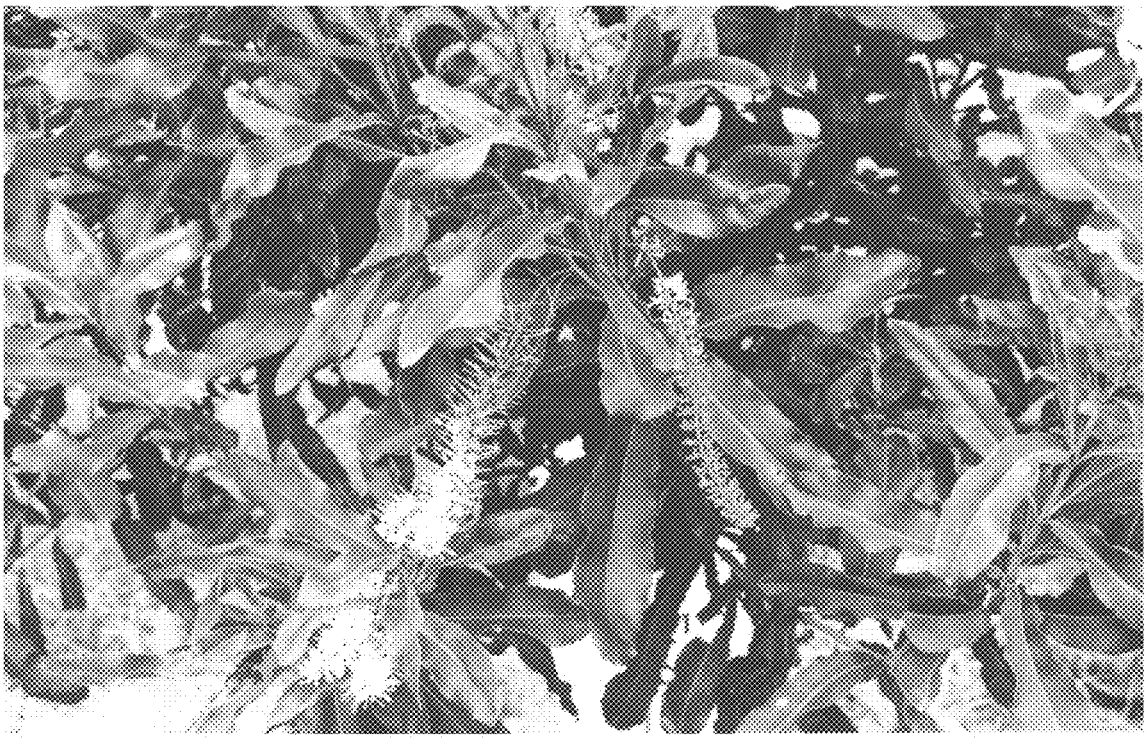
FIG. 4 shows leaves and flowers of an 'MCT1' *macadamia* tree.
Figure 5:
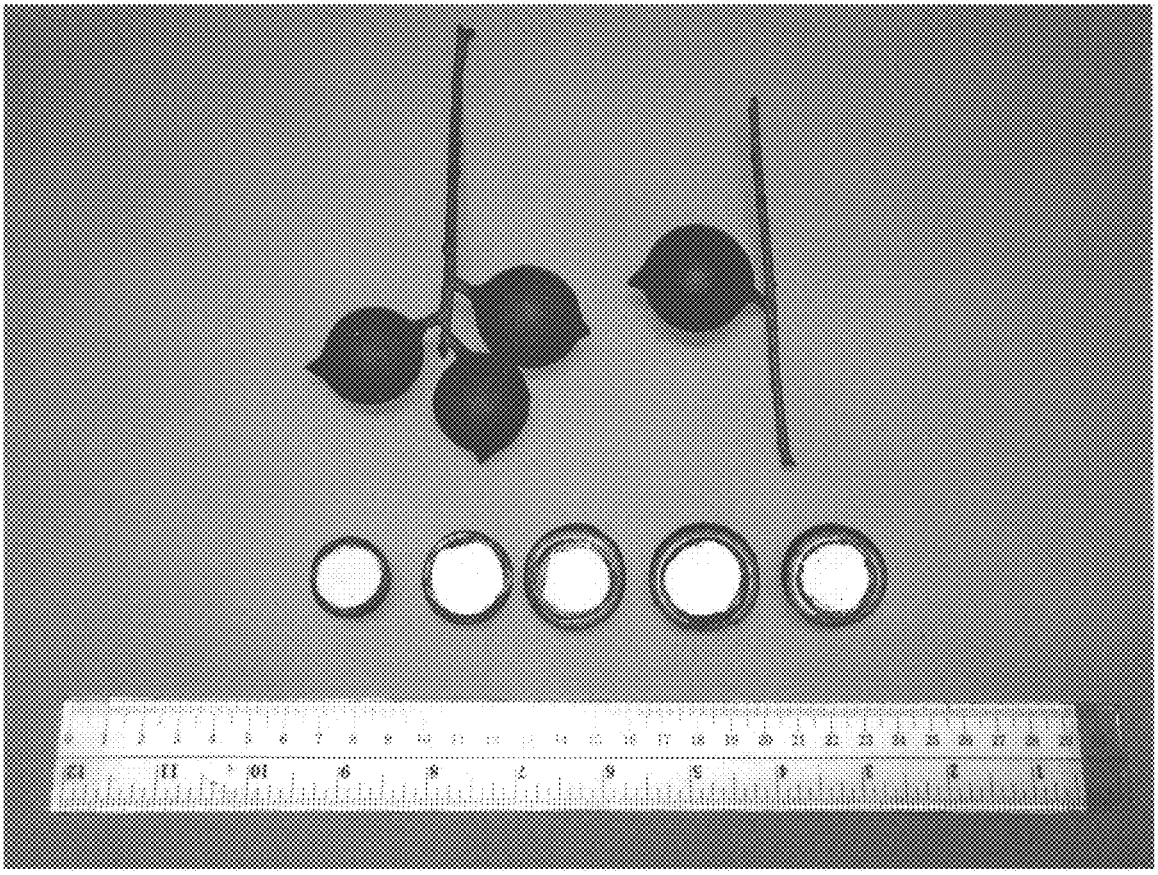
FIG. 5 shows unopened and sectioned 'MCT1' fruit.
Figure 6:
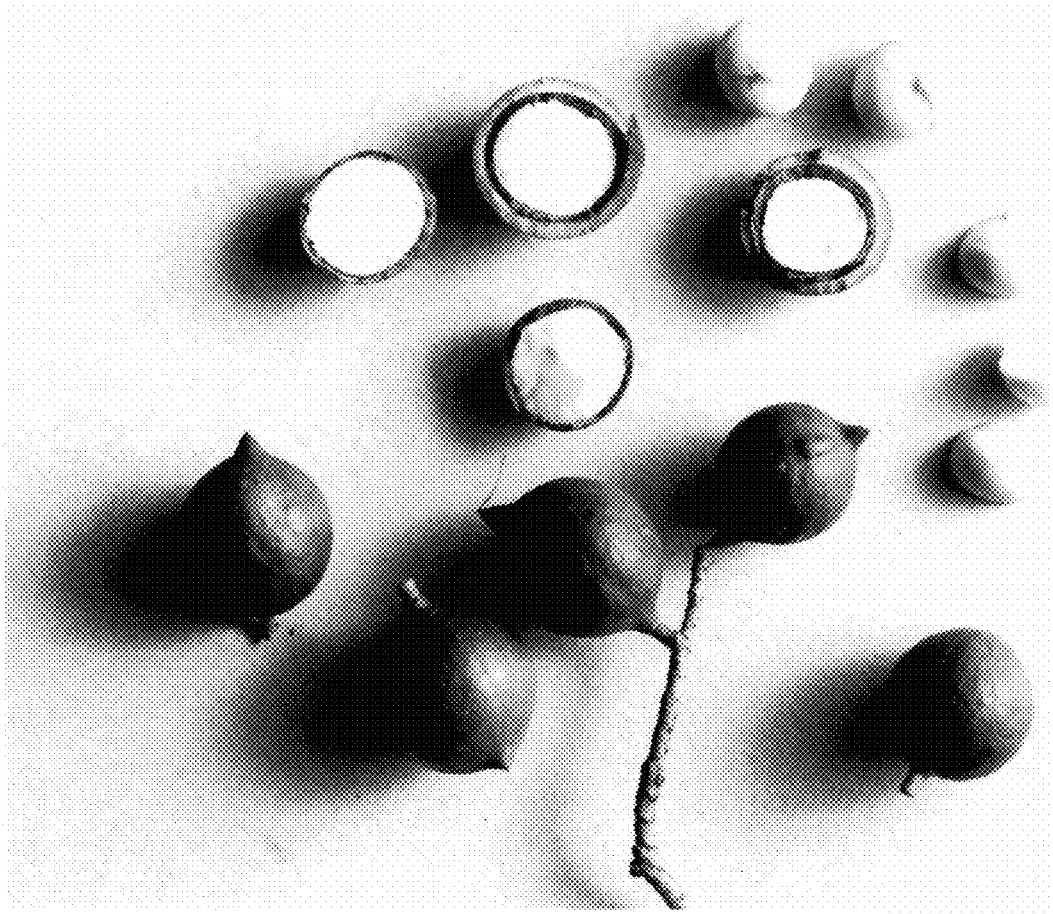
FIG. 6 shows unopened and sectioned 'MCT1' fruit, and 'MCT1' *macadamia* nuts (kernels) with husk and shell removed.

Tree:

*Vigor*.—Medium to High.
*Habit*.—Spreading.
*Height*.—Medium; 9-year-old tree 5 m (see FIG. 1); mature tree 10 m.
*Spread*.—Medium; 9-year-old tree 3.5 m (see FIG. 1); mature tree 7 m.
*Canopy density*.—Slightly dense.
*Trunk diameter* (*at* 30 *cm above the graft*).—34.6 mm to 40.7 mm.
*Bark texture*.—Smooth.
*Bark color*.—Yellow-green 147A.

Branch (fruiting branches located at around 1 m above the graft union):

*Length*.—2.5 m to 3.0 m.
*Diameter*.—30 mm to 35 mm.
*Attitude*.—Intermediate.
*Crotch angle*.—45°.
*Bark color*.—Yellow-green 147A.

One year old shoot:

*Color*.—Light brown 200D.
*Pubescence*.—Absent.
*Thickness*.—6 mm to 8 mm.
*Internode length*.—50 mm to 75 mm.

Flower buds:

*Quantity per spur*.—Medium.
*Shape*.—Cylindrical.
*Length*.—9 mm to 12 mm.
*Diameter*.—1 mm to 2 mm.
*Color*.—Creamy white 155D.

Inflorescence (raceme):

*Length*.—Medium, 120 mm to 180 mm.
*Diameter*.—15 mm to 25 mm.
*Density of flowers on inflorescence*.—Medium.
*Density of inflorescences on tree*.—Medium.
*Attitude*.—Horizontal to drooping.
*Size of flowers*.—Medium.
*Color of flowers*.—Creamy white 155D.
*Time of flowering*.—September.
*Duration of flowering*.—3 to 4 weeks.
*Fruits per inflorescence*.—5 to 20.

Leaves:

*Shape*.—Oblanceolate.
*Length*.—Medium, 120 mm to 200 mm.
*Width*.—Medium, 50 mm.
*Length/width ratio*.—Medium, 2.5:1 to 4:1.
*Blade margin*.—Slightly wavy, spines at base diminishing toward tip.
*Relative number of spines on margin*.—Many.
*Apex*.—Apiculate.
*Base*.—Acute.
*Texture and sheen of upper surface*.—Smooth, dull.
*Young leaf*.—Color of upper surface — Dark green 136B.
*Young leaf*.—Color of lower surface — Medium green 141A.
*Young leaf*.—Color of vein upper surface — Yellow green 144A.
*Young leaf*.—Color of vein lower surface — Yellow green 144B.
*Mature leaf*.—Color of upper surface — Dark green 137A.
*Mature leaf*.—Color of lower surface — Medium green 141B.
*Mature leaf*.—Color of vein upper surface — Yellow green 144A.
*Mature leaf*.—Color of vein lower surface — Yellow green 144B.
*Attitude in relation to shoot*.—Slightly upward, 30°.
*Curvature of longitudinal axis*.—Slight.

Petiole:

*Presence of petiole*.—Present.
*Length*.—Medium, 8 mm to 12 mm.
*Diameter*.—2 mm.
*Color*.—Yellow green 144A.

Fruit:

*Husk color*.—Medium green 141B.
*Husk thickness*.—Thin, 2 mm.
*Presence of neck*.—Present.
*Relative size of apical point*.—Large.

Nut shell:

*Height*.—Medium, 20 mm to 30 mm.
*Width*.—Medium, 20 mm to 30 mm.
*General shape in profile*.—Circular.
*Shell surface texture*.—Smooth.
*Shell thickness*.—Thin, 2 mm.
*Shell color*.—Brown 165A.
*Presence of pale specks on shell surface*.—Present.
*Conspicuousness of suture*.—Weak to inconspicuous.
*Suture color*.—Brown 165A.

Kernel:

*Shape*.—Round and slightly flattened.
*Length*.—Medium, 18 mm to 24 mm.
*Width*.—Medium, 12 mm to 18 mm.
*Color*.—Off-white 155B.
*Discoloration of distal half of kernel*.—Absent.

Harvest:

*Harvest date range*.—Late April to August; primary harvest window is June and July (winter, Southern Hemisphere).
*Amount of fruit produced per tree per harvest*.—See Table 2.

TABLE 2

'MCT1' Productivity

| | Nut in Shell (NIS) Weight | Total Kernel Recovery (TKR) (Kernel weight % of NIS) |
|---|---|---|
| 3.5 years after planting | 3.0 kg | 45% |
| 4.5 years after planting | 6.7 kg | 49% |
| 5.5 years after planting | 9.1 kg | 44% |

Disease resistance/susceptibility: Tolerant to husk spot (*Pseudocercospora macadamiae*) and the tendency to Abnormal Vertical Growth (AVG).

Pest resistance/susceptibility: Unknown.

Market use: Fresh and processed (dried) nuts.

Storage characteristics: Satisfactory shelf life.

I claim:

1. A new and distinct *macadamia* tree substantially as described and illustrated herein.

* * * * *